(12) United States Patent
Fowler et al.

(10) Patent No.: US 6,916,646 B1
(45) Date of Patent: Jul. 12, 2005

(54) ENTEROBACTERIACEAE FERMENTATION STRAINS

(75) Inventors: Timothy Fowler, San Carlos, CA (US); Stuart C. Causey, Palo Alto, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 08/876,132

(22) Filed: Jun. 23, 1997

(51) Int. Cl.$^7$ ............................. C12N 1/36; C12N 1/20
(52) U.S. Cl. .................. 435/245; 435/252.1; 435/252.8
(58) Field of Search .................... 435/245, 252.1–252.8

(56) References Cited

U.S. PATENT DOCUMENTS

| | | | |
|---|---|---|---|
| 3,790,444 A | 2/1974 | Oga et al. ................... | 435/137 |
| 4,683,195 A | 7/1987 | Mullis et al. .................. | 435/6 |
| 4,696,897 A | * 9/1987 | Sonoyama et al. ........... | 435/42 |
| 4,800,195 A | 1/1989 | Burgess et al. ............. | 514/150 |
| 4,965,188 A | 10/1990 | Mullis et al. .................. | 435/6 |
| 5,008,193 A | 4/1991 | Anderson et al. ........... | 435/138 |

OTHER PUBLICATIONS

ATCC Catalog Accession No. 31626.*
ATCC Catalog Accession No. 31628.*
Frey et al., The Molecular biology of IncQ plasmids. In: Thomas (Ed.), Promiscuous Plasmids of Gram Negative Bacteria. Academic Press, London, pp. 79–94. (1989).
Kageyama et al., "*Pantoea punctata* sp. nov., *Pantoea citrea* sp. nov., and *Pantoea terrea* sp. nov. Isolated from Fruit and Soil Samples," *International Journal of Systematic Bacteriology*, vol. 42, p. 203–210, 1992.
Lazarus et al., "Metabolic and Genetic Aspects of a Recombinant Bioconversion Leading to Ascorbic Acid," *Proceedings 6$^{th}$ International Symposium on Genetics of Industrial Microorganisms*, Strasbourg, vol. II 1073–1082, 1990.
Maniatis, "Phagemids: Plasmids Containing an Origin of Replication Derived from a Filamentous Bacteriophage," *Single Stranded, Filamentous Bacteriophage Vectors*, chapter 4 pp. 17–25 (1989) GC506.
Truesdell et al., "Pathways for Metabolism of Ketoaldonic Acids in an *Erwinia* sp.", *Journal of Bacteriology*, Nov. 1991, V. 173:21 pp. 6651–6656 (GC558).
Anderson, S. et al., "Production of 2–Keto–L–Gulonate, an Intermediate in L–Ascorbate Synthesis, by a Genetically Modified *Erwinia herbicola*," *Science*, vol. 230, Oct. 11, 1985, pp. 144–149.
Bilic, M. et al., "Construction of Plasmid Vectors for Cloning 2,5– Diketo–D–Gluconate Reductase Gene in Genus *Erwinia*," Annual Meeting of Croatian Biochemists, 17018 Lipnja 1993, pp 105.
Bilic, M et al., "Cryptic Plasmids from the Genus *Erwinia* in Construction of Stabile Bifunctional Vectors for *Escherichla* and *Erwinia*," *PLIVA Research Institute*, P1–18, year unknown.

Bilic, M. et al., "Isolation and characterization of a cryptic plasmid from *Erwinia citreus* ATCC 31623," *J. of Applied Microbiology*, V. 83, pp. 485–492, 1997.

Bilic M. et al., "Characteristics of Two Types of in vitro Constructed Plasmid Vectors for Bacterium *Erwinia citreus*", *Prehrambeno–tehnol. Biotehnol.*, rev. 33 (1) pp. 13–18 (1995).

Cha, J. et al, "Identification and Characterization of a *Pantoea citrea* Gene Encoding glucose Dehydrogenase That Is Essential for Causing Pink Disease of Pineapple," *Applied and Environmental Microbiology*, vol. 63, No. 1, Jan. 1997, pp. 71–76.

Deliae, V. et al. "Study, Construction and Cloning in Organisms for Conversion of Glucose to Ketoacids," *Ministry of Science and technology, Svibor—Collecting Data on Projects in Croatia*, Project Code: 1–08–045, Jan. 1, 1991 to Dec. 15, 1995—Internet Disclosure.

Frey, J. et al., "Replication and copy number control of the broad–host–range plasmid RSF1010," *Gene.*, vol. 113, (1991) pp. 101–106.

Grindley, J. F. et al., "Conversion of Glucose to 2–Keto–L–Gulonate, an Intermediate in L–Ascorbate Synthesis, by a Recombinant Strain of *Erwinia citreus,*" *Applied and Environmental Microbiology*, vol. 54, No. 7, Jul. 1988, p. 1770–1775.

Mamic, S. et al., "Stability of Constructed Plasmids in Genus *Erwinia*," *PLIVA Research Institute*, P1–18, Year Unknown.

Miller, J. H., "Experiments in Molecular Genetics," *Society of Fellows, Harvard University*, Cold Spring Harbor Laboratory (1972), pp. 104–106.

* cited by examiner

*Primary Examiner*—David Guzo
*Assistant Examiner*—Daniel M. Sullivan
(74) *Attorney, Agent, or Firm*—Genencor International, Inc.

(57) ABSTRACT

Methods are provided for preparing improved fermentation strains of the family Enterobacteriaceae which comprise the steps of eliminating the cryptic plasmid from the progenitor strain thereby creating the improved strain. Methods for reducing the mobilization properties of resident plasmids in an Enterobacteriaceae strain containing a cryptic plasmid are also provided. The present invention provides the nucleic acid sequence of pS, a cryptic plasmid found in *Pantoea* which can be used to identify the cryptic plasmid in strains of Enterobacteriaceae.

16 Claims, 12 Drawing Sheets

```
AGATCTACACAAGGCAAATTGAAAAAATAGATAAAATTTCGCAGGTATTAAAGCCGACTTAAAACAAATGAGTGAAGAA
----+----+----+----+----+----+----+----+----+----+----+----+----+----+----+----  80
TCTAGATGTGTTCCGTTAACTTTTTATCTATTTTAAAAGCGTCCATAATTCGGCTGAATTTGTTACTCACTTCTT

GAAAAGAAAAAATACATATTTGAGTTAGTAAAAGAGAAAAATAAAGAAGACCTCGGCTTAACAGTCGA
----+----+----+----+----+----+----+----+----+----+----+----+----+----+----+----  160
CTTTTCTTTTTTATGTATAAACTCAATCATTTCTCTTTTATTTCTCTGGAGCCGAATTGTCAGCT

AAAACCAGAAATAATAAAAAGAAAGAGACTGTGATTTTTAATGGAAATCGTGAGGAAAAGAAATTTTAATTTTCATTT
----+----+----+----+----+----+----+----+----+----+----+----+----+----+----+----  240
TTTTGGTCTTTATTATTTTCTTTCTCTGACACTAAAAATTACCTTTAGCACTCCTTTCTTTAAAATTAAAAGTAAAA

CGAGGGATTAATTGTTGTAAGTTGATGAAAAATCTAGATAAAAATGCAGATCAAAAATGTGTTGAATTTGACATTATT
----+----+----+----+----+----+----+----+----+----+----+----+----+----+----+----  320
GCTCCCTAATTAAACAACATTCAACTTTTAGATCTATTTTTACGTTTTACACAACTTAAACTGTAATAA

GAAATACGTAGTATATCAATAATGGGGTTTGTCTATTTTATTTGCGAAGATTGAAATCTGAGTGAAGAAATAGTT
----+----+----+----+----+----+----+----+----+----+----+----+----+----+----+----  400
CTTTATGCATCATATAGTTATTACCCCAAACAGATAAAATAAACGCTTCTAACTTTAGACTCACTTTCTTTATCAA

TGCGAGAGCAAAAACCCTTGCCGTTTTTTCAAATGACTTTGGAAAAATTCATTGTGAGCGGTAGCGAAACTTTGAA
----+----+----+----+----+----+----+----+----+----+----+----+----+----+----+----  480
ACGCTCTCGTTTTTTGGGAACGGCAAAAAAGTTTACTGAAACCTTTTTAAGTAACACTCGCTTTGAAACTT
```

FIG. 1A-1

```
ATTTTTTACATTGGAAATTTGAAAAATAAGGCAAAAGAAACTCAAATGGAAAAAATATTATTAAAAAAAGGAGATCG
     ----+----+----+----+----+----+----+----+----+----+----+----+----+----+----  560
TAAAAAATGTAACCTTTAAACTTTTTATTCCGTTTTCTTTGAGTTTACCTTTTTATAATAATATTTTTCCTCTAGC

Asn Phe Leu His Trp Lys Phe Glu Lys Ile Arg Gln Lys Lys Leu Lys Trp Lys Tyr Tyr Lys Lys Arg Arg Ser

GATATGGATTTTAAAAGCAGAAACTGACATTGAATGAAAAAAATCTATGCTGAGAGTGAATTAAA
     ----+----+----+----+----+----+----+----+----+----+----+----+----+----+----  640
CTATACCTAAAATTTTCGTCTTTTGACTGTAACTTACTTTTTTTAGATACGACTCTCACTTAATTT

Asp Met Asp Phe Lys Ser Arg Lys Leu Thr Leu Asn Glu Lys Lys Asp Leu Glu Lys Ile Tyr Ala Glu Ser Glu Lys

AGCAAAAAAATTGGGAACTCAACCCGGTGTTTGTTTTAGAAATGACGATGAAAGAAATGATGAAATATCAACCTCGATG
     ----+----+----+----+----+----+----+----+----+----+----+----+----+----+----  720
TCGTTTTTTTAACCCTTGAGTTGGGCCACAACAAATCTTTACTGCTACTTCTTACTACTTTTATAGTTGGAGCTAC

Ala Lys Lys Leu Gly Thr Gln Pro Gly Val Val Leu Glu Met Thr Met Lys Glu Met Met Lys Asn Ile Asn Leu Asp

TTAATGAAGAAACAGCAGGTCAATATAGGAATTATTCAAAAATAAGTTGAGCATAGTAAATCAGATGATCTAGTAACG
     ----+----+----+----+----+----+----+----+----+----+----+----+----+----+----  800
AATTACTTCTTTGTCGTCCAGTTATATCCTTAATAAGTTTTATTCAACTCGTATCATTAGTCTACTAGATCATTGC

Val Asn Glu Glu Thr Ala Gly Gln Tyr Arg Lys Leu Phe Lys Asn Lys Val Glu His Ser Lys Ser Asp Leu Val Thr
```

FIG._1A-2

```
GGACTATTAGAGTGTGGAACTCGAAATAGTTTTGATAAAACAAGAAGTGCCTTTCGTTTTTGTATTTGTGAGAGAATTCA
                                                                                880
CCTGATAATCTCCACACCTTGAGCTTTATCAAAACTATTTGTTCTTCACGGAAAGCAAAACATAAACACTCTCTTAAGT
Gly Leu Leu Glu Cys Gly Thr Arg Asn Ser Phe Asp Lys Thr Arg Ser Ala Phe Arg Cys Ile Cys Glu Arg Ile Gln

GCAACTGAGAAAGAAGCTGATAATGCAAGAGTAAAAGATTTCGATACAATGAAAGCAAAACTAAAGAGGCTTTTG
                                                                                960
CGTTGACTCTTTTCTTCGACTATTACGTTCTCTCATTTTCTAAAGCTATGTTACTTTCGTTTTTGATTCTCCGAAAAC
Gln Leu Arg Lys Glu Ala Asp Asn Ala Arg Val Lys Asp Phe Asp Thr Met Lys Ala Lys Thr Lys Glu Ala Phe

AATTGAGTTTTGTTTTGATAAGGATTTTTTGAGTGAAAATAGAATTCAATGGAATGATATTTCTCACAACAAAAAGAC
                                                                                1040
TTAACTCAAAACAAAACTATTCCTAAAAAACTCACTTTTATCTTAAGTTACCTTACTATAAAGAGTGTTGTTTTTCTG
Asn Leu Ser Phe Val Phe Asp Lys Asp Phe Leu Ser Glu Asn Arg Ile Gln Trp Asn Asp Ile Ser His Asn Lys Lys Asp

TCTGCAAGTAAAAGAAAAACAATGAAAGAAGCGGACACAATGGATGATATTTTTAAGAGGCTAAAAAATAATAAATCTAC
                                                                                1120
AGACGTTCATTTTCTTTTGTTACTTTCTTCGCCTGTGTTACCTACTATAAAAATTCTCGATTTTTATTATTTAGATG
Ser Ala Ser Lys Arg Lys Thr Met Lys Glu Ala Asp Thr Met Asp Asp Ile Phe Lys Arg Leu Lys Asn Asn Lys Ser Thr

ATATGATCGTTATGCTGGATTCCTTTCTATTGTTCGATTACAGGTTGCAGACCAGAAGTTTAAAGGGTATAGAGA
                                                                                1200
TATACTAGCAATACGACCTAAGGAAAGATAAACAAGCTAATGTCCAACGTCTGGTCGTCTTCAAAATTTCCCATATCTCT
Tyr Asp Arg Tyr Ala Gly Phe Leu Ser Ile Cys Ser Ile Thr Gly Cys Arg Pro Ala Glu Val Leu Lys Gly Ile Glu
```

FIG._1B-1

Tyr Asp Arg Tyr Ala Gly Phe Leu Ser Ile Cys Ser Ile Thr Gly Cys Arg Pro Ala Glu Val Leu Lys Gly Ile Glu
TAGTAAGAAACAGATATGAGGATGGTATATCTTTTAAAATACTTGGTGCAAAGGTTGGAAATGACAGAGGGCAAAGCGAA
ATCATTCTTTGTCTATACTCCTACCATATAGAAAATTTATGAACCACGTTTCCAACCTTTACTGTCTCCCGTTTCGCTT  1280

Ile Val Arg Asn Arg Tyr Glu Asp Gly Ile Ser Phe Lys Ile Leu Gly Ala Lys Val Gly Asn Asp Arg Gly Gln Ser Glu
AGAACATTACATTTTGATTTATCAAAATATCATGATAATGAGCAAATGAATTATATTTTGTCGCAATTAAAAGATAATAA
TCTTGTAATGTAAAACTAAATAGTTTTATAGTACTATTACTCGTTACTTAATATAAAACAGCGTTAATTTTCTATTATT  1360

Arg Thr Leu His Phe Asp Leu Ser Lys Tyr His Asp Asn Glu Gln Met Asn Tyr Ile Leu Ser Gln Leu Lys Asp Asn Lys
ATTTTCTACAAACCAGATGGGAAGCTCTACAACAGCTTGAGGCAATACCCTCTACATCCAACATAGAACGTTTCACTGT
TAAAAGATGTTTGGTCTACCCTTCGAGAGTTGTCGAACTCCGTTATGGGAGATGTAGGTTGTATCTTGCAAAGTGACA   1440

Phe Phe Tyr Lys Pro Asp Gly Lys Leu Tyr Asn Ser Leu Arg Gln Tyr Leu Tyr Ile Gln His Arg Thr Phe Ser Leu
ATACACTTCGTCACAGGGTTGCGAGTGATCTCAAGGCATCCGGTGCAGATGACTTCACCATAGCGGCTNTTTTGGGTCAC
TATGTGAAGCAGTGTCCCAACGCTCACTAGAGTTCCGTAGGCCACGTCTACTGAAGTGGTATCGCCGANAAACCCAGTG  1520

Tyr Thr Leu Arg His Arg Val Ala Ser Asp Leu Lys Ala Ser Gly Ala Asp Asp Phe Thr Ile Ala Ala ??? Leu Gly His

FIG._1B-2

```
AGAGTGACTCAAAGCCAGGAGTTACTACGGCTATGCTCGTTCGTCGNAAGGTGGTATCGCTGTAACTGGTGTTGAGTGCT
                                                                              1600
                                                                              ─┼─
TCTCACTGAGTTTCGGGTCCTCAATGATGCCGATACCGAGCAAGCAGCNTTCCACCATAGCCGACATTGACCACAACTCACGA

Arg Val Thr Gln Ser Gln Glu Leu Leu Arg Leu Cys Ser Phe Val ??? Arg Trp Tyr Arg Cys Asn Trp Cys

CTGATGTTGTGAAAGCAAACAAGAGTCAGTTNGCTGTATCAAGGACTCCGAGCCAGATCT
                                                         1660
                                                         ─┼─→
GACTACAACACTTTCGTTTGTTCTCAGTCAANCGACATAGTTCCTGAGGCTCGGTCTAGA
```

FIG._1C

```
AGATCTCAACCAGTTTAAAATCGCACTTCAAGAAGTAAAAATAGGGGCCGGCACCGGCTCTTTTTTGGTGTTTTGTAG
                                                                              80
TCTAGAGTTGGTCAAATTTAGCGTGAAGTTCTTCATTTTATCCCGGCCGTGGCCGAGAAAAACCACAAAAACATC

TTAGTGGATATATCTGTTAGCTACAGAGAAAAGCGATTTTAGAGGGTTTGACGAGGTTTTTCGAGCTATCCAGGGTTT
                                                                              160
AATCACCTATATAGACAATCGATGTCTCTTTTTCGCTAAAATCTCCAAAAGCTCCAAAAAGTCGATAGGTCCCAAAA

TGGGTTTTTGGGGTTGGATCAGAGAAAGTCGTTCAAGATTATTGACATAAAGACAGGAAGGTTTATAACAAGTACCAGATA
                                                                              240
ACCCAAAAACCCCAACCTAGTCTTTTCAGCAAGTTCTAATAACTGTATTTCTGTCCTTCCAAATATTGTTCATGGTCTAT

CGACAAAACCAGCTTTGCAGGCTGGCTTTGAAGGACTAAAAGAGAAGTGGGGACTTCTTTGAGTCTCTTGTAATCAAGTTGGTC
                                                                              320
GCTGTTTGGTCGAAACGTCCGACCGAACTTCCTGATTTCTTCACCCCTGAAGAAACTCAGAACATTAGTTCAACCAG

AGAACTCGATTACGATTTGTAAGTAGAAATCTAACTCACATTTCGCAGAAGTCAAACTTACCTCTTAGTTACAACTCAA
                                                                              400
TCTTGAGCTAATGCTAAACATTCATCTTTAGATTGAGTGTAAAGCGTCTTTCAGTTTGAATGGAGAATCAATGTTGAGTT

AAATTTCCTAGCCTTTTCAGATCCTTAAGCATACATATTTTGTTAAACCGATTGTGTCCGGTGTTGGTGTGGAGCCAT
                                                                              480
TTTAAAGGATCGGAAAGTCTAGGAATTCGTATGTGTATAAAACAAATTTGGCTAACACAGGCCACAAACCACACCTCGGTA
```

*FIG. 1D-1*

```
TGATCCGAGTGGTCAATATGTGATTGTTCGCCAAACAGTGTATGTAGGTCTAAACGGGAGTGCTACAAAAGACCATACC    560
ACTAGGCTCACCAGTTATACACTTAACAAGGGTTTGTCACATACCAGATTTGCCCCTCACGATGTTTTCTGGTATGG

CGAAACGAGTGCCTAAGTGTTTTGGTTATCAACCAGGTAAGCTATGAGAAAGCCCAGCCATAAATGGGGTTAGGTTGAAG    640
GCTTTGCTCACGGATTCACACAAACCAATAGTGGTCCATTCGATACTCTTTCGGGTATTACCCCAATCCAACTTC

CAAGTCTTCATATGGTGCGACACAAGGGGTGTAGTAGGGTGTCGTCAAACTGAAAGGTTTGATAGCTCTAAGCTTGTGCT    720
GTTCAGAAGTATACCACGCTGTGTTCCCCACATCATCCCACAGCAGTTTGACTTTCCAAACTATCGAGATTCGAACACGA

TCTGTGGGTCAAGCCTCAAGTGCTCACCTGATCTGTGGTGTCGTCTACCTGATAACTTTCACTTTTTCGAGTGAAATTCAGGAGG    800
AGACACCCAGTTCGGAGTTCACGAGCCCAGCTTTGCGGGGTTCGGCACACATCCAGCTTACAGCATTGGTGTCTCTTGCGAAGCTGAAGC

CGAAACTATGGGTCAAGCCCCAGTTCGGGTCGAAACGACCCCAAGCGTGTAGGTCGAATGTCGTAACCACGAGAACGCTTCGAAGC    880
GCTTTGATACCCAGTTCGGGTCGAAACGACCCCAAGCGTGTAGGTCGAATGTCGTAACCACGAGAACGCTTCGACTTCG
```

FIG._1D-2

```
ACAAAAATCTAATCCAGGGTTTGGGTTTTTATACCAGAAGCAAACAAAAAAATAAAACAAAGAAAAATTTTCGAGCGA    960
         ----+----|----+----|----+----|----+----|----+----|----+----|----+----|----+----|
TGTTTTTAGATTAGGTCCCAAACCCAAAATATGGTCTTCGTTTTGTTTTTTATTTGTTTCTTTTAAAAGCTCGCT

AAAATATTTGGAATTTTTAAAGGCGATACTTGCTACCGCACTTTTGCCATATTTAAAACCTGACTATCTTTATAAGT    1040
         ----+----|----+----|----+----|----+----|----+----|----+----|----+----|----+----|
TTTTATAAACCTTAAAAATTTCCGCTATGAACGATGGCGTGAAAATTTGGACTGATAGAAATATTCA

TAATAGATATCCGTTAGATTATAAGTATGTTAAAAACGAGTAAAAACAATAACTTATATATTAATTCTGAATTATA    1120
         ----+----|----+----|----+----|----+----|----+----|----+----|----+----|----+----|
ATTATCTATATAGGCAATCTAATATTTCATACAATTTTGCTCATTTTGTTATTGAATATATAAATTAAGACTTAATAT

TTTGACAGTGATTATTTAATATATTAAGAGATATATCTATTAGCTTAAATATAACTAAAAAAGAGGTAAATATATGGAT    1200
         ----+----|----+----|----+----|----+----|----+----|----+----|----+----|----+----|
AAACTGTCACTAATAAATTATATAATTCTATATAGATAATCGAATTATATTGATTTTTTCTCCATTATATACCTA

TGTGTATTTAAAAAAGCATTAGAAATGAAATAGAACATTATAAAAAAGACGGTGATATCAAATCTTTCTTACAATACTT    1280
         ----+----|----+----|----+----|----+----|----+----|----+----|----+----|----+----|
ACACATAAATTTTCGTAATCTTTACTTTGTAATATTTTCTGCCACTATAGTTTAGAAAGAATGTTATGAA

GCATTACTTTGATATAGATAAAGCATTAAATGGTGATGAATGTGGGCGATATTATAAACTCAAATTTATCCATTGATGAAA    1360
         ----+----|----+----|----+----|----+----|----+----|----+----|----+----|----+----|
CGTAATGAAACTATATCTATTTCGTAATTACCACTACTTACCGCTATAATATTTGAGTTTAAATAGGTAACTACTTT
```

FIG._1E-1

```
GTTTGATCTTCTTGATGTTGAGCACAATTTCGGCTGGGCTTTCAATAAAATAATACAGAGACGAAATGAATATTTATCA    1440
CAAAACTAGAAGAACTACAACTCGTGTTAAAGCCGACCCGAAAGTTATTTATTGTCTCTGCTTTACTTATAAATAGT

TCAGCTAAAACTGAAAATGATTTTAAAAAATACTCGTTCTTTATTCATTGGATCAATTGGGAAGAATTTAATTACGATGA    1520
AGTCGATTTTGACTTTTACTAAAATTTTTATGAGCAAGAATAAGCTAGTTAACCCTTCTTAAATTAATGCTACT

GATGAGTACAATACATCAAGAAATGATTAGATAATTACACATATGGAGAAATAACCATATGAATAATAAAAT    1600
CTACTCATGTTATGTAGTTCTTACTAATTCCTAATCTATTAATGTGTATACCCTCTTATTGGTATACTTATTTTA

AAGAGAATATATTGATTTCGAAATAACAAAAGATATAAAAGAAAGTCAGCTCTTAAAAATATCTGCATTGATCGATGTTT    1680
TTCTTATATAACTAAAGCTTTATTGTTTCTATATTTTCTTCAGTCGAGAATTTTTATAGACGTAACTAGCTACAAA

TAAAAGTAGATGAAAATTTATTGATGAAGAGGATTTGCAACTAAAGATATATTGAAAATATCGTATGAAAATCCTATTGAT    1760
ATTTTCATCTACTACTTTTAAATAACTACTTCTCCTAAACGTTGATTTCTATAACTTTTATAGCATACTTTTAGGATAACTA

GATCCAGATGATGGCATAAGAAAATCACAATTCGCACGAAGAAATGCCTATGCTTTCCGCATTAAAAAAACAAGCAAAAA    1840
CTAGGTCTACTACCGTATTCTTTAGTGTTAAGCCGTGCTTCTTTACGGATACGAAAGGCGTAATTTTTTGTTCGTTTTT
```

*FIG._1E-2*

```
GAGATCT
         → 1847
CTCTAGA
```

FIG._1F

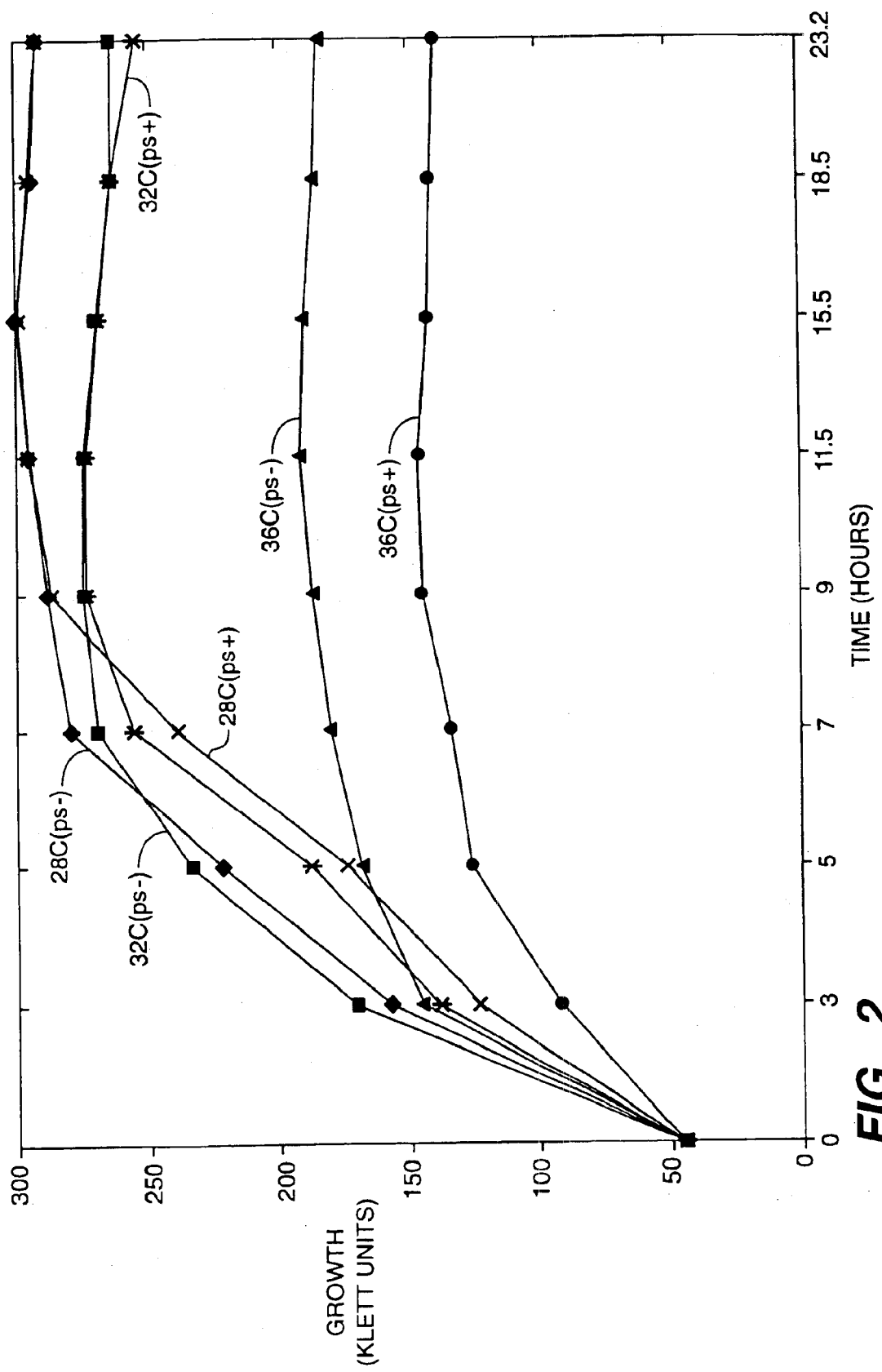
FIG._2

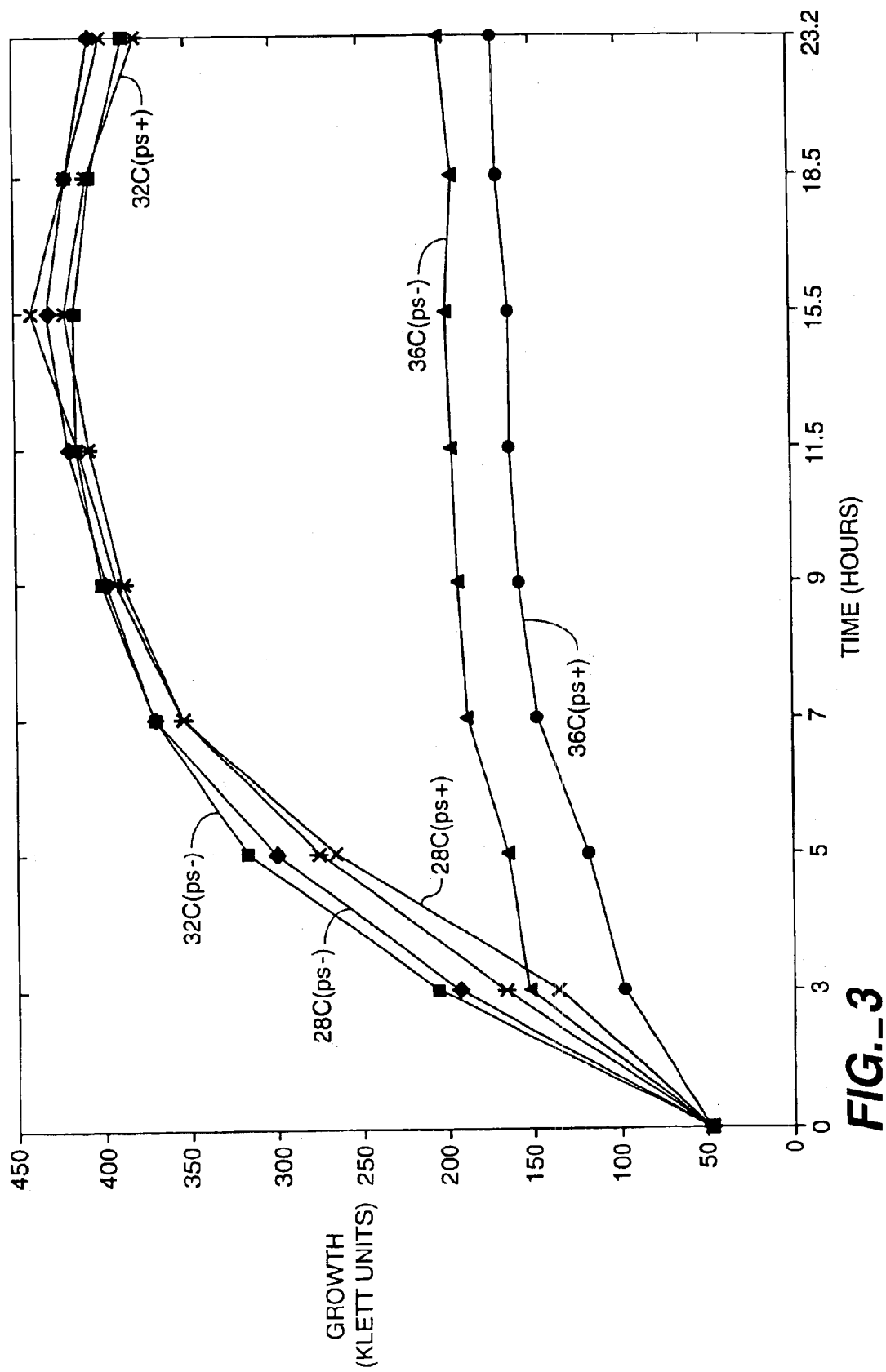
FIG._3

```
                           SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
          (A) LENGTH: 1660 base pairs
          (B) TYPE: nucleic acid
          (C) STRANDEDNESS: single
          (D) TOPOLOGY: linear (xi) SEQUENCE DESCRIPTION: SEQ ID NO:1:

AGATCTACAC AAGGCAAATT GAAAAAATAG ATAAAATTTT CGCAGGTATT AAAGCCGACT     60

TAAAACAAAT GAGTGAAGAA GAAAAGAAAA AAATAAATAC ATATTTTGAG TTAGTAAAAG    120

AGAAAGAAAA AATAAAAGAA GACCTCGGCT TAACAGTCGA AAAACCAGAA ATAATAAAAA    180

GAAAGAGACT GTGATTTTTA ATGGAAATCG TGAGGAAAAG AAAATTTTAA TTTTCATTTT    240

CGAGGGATTA ATTTGTTGTA AGTTGATGAA AAATCTAGAT AAAAAATGCA GATCAAAAAT    300

GTGTTGAATT TGACATTATT GAAATACGTA GTATATCAAT AATGGGGGTT TGTCTATTTT    360

ATTTTGCGAA GATTGAAAAT CTGAGTGAAA GAAAATAGTT TGCGAGAGCA AAAAAACCCT    420

TGCCGTTTTT TTCAAATGAC TTTGGAAAAA ATTCATTGTG AGCGGTAGCG AAACTTTGAA    480

ATTTTTTACA TTGGAAATTT GAAAAAATAA GGCAAAAGAA ACTCAAATGG AAAAAATATT    540

ATTATAAAAA AAGGAGATCG GATATGGATT TTAAAAGCAG AAAACTGACA TTGAATGAAA    600

AAAAAGATTT GGAAAAAATC TATGCTGAGA GTGAATTAAA AGCAAAAAAA TTGGGAACTC    660

AACCCGGTGT TGTTTTAGAA ATGACGATGA AAGAAATGAT GAAAAATATC AACCTCGATG    720

TTAATGAAGA AACAGCAGGT CAATATAGGA AATTATTCAA AAATAAAGTT GAGCATAGTA    780
```

```
AATCAGATGA TCTAGTAACG GGACTATTAG AGTGTGGAAC TCGAAATAGT TTTGATAAAA      840

CAAGAAGTGC CTTTCGTTTT TGTATTTGTG AGAGAATTCA GCAACTGAGA AAAGAAGCTG      900

ATAATGCAAG AAGAGTAAAA GATTTCGATA CAATGAAAGC AAAAACTAAA GAGGCTTTTG      960

AATTGAGTTT TGTTTTTGAT AAGGATTTTT TGAGTGAAAA TAGAATTCAA TGGAATGATA     1020

TTTCTCACAA CAAAAAAGAC TCTGCAAGTA AAGAAAAAC AATGAAAGAA GCGGACACAA     1080

TGGATGATAT TTTTAAGAGG CTAAAAAATA ATAAATCTAC ATATGATCGT TATGCTGGAT     1140

TCCTTTCTAT TTGTTCGATT ACAGGTTGCA GACCAGCAGA AGTTTTAAAG GGTATAGAGA     1200

TAGTAAGAAA CAGATATGAG GATGGTATAT CTTTTAAAAT ACTTGGTGCA AAGGTTGGAA     1260

ATGACAGAGG GCAAAGCGAA AGAACATTAC ATTTTGATTT ATCAAAATAT CATGATAATG     1320

AGCAAATGAA TTATATTTTG TCGCAATTAA AAGATAATAA ATTTTTCTAC AAACCAGATG     1380

GGAAGCTCTA CAACAGCTTG AGGCAATACC TCTACATCCA ACATAGAACG TTTTCACTGT     1440

ATACACTTCG TCACAGGGTT GCGAGTGATC TCAAGGCATC CGGTGCAGAT GACTTCACCA     1500

TAGCGGCTNT TTTGGGTCAC AGAGTGACTC AAAGCCAGGA GTTACTACGG CTATGCTCGT     1560

TCGTCGNAAG GTGGTATCGC TGTAACTGGT GTTGAGTGCT CTGATGTTGT GAAAGCAAAC     1620

AAGAGTCAGT TNGCTGTATC AAGGACTCCG AGCCAGATCT                            1660

(2) INFORMATION FOR SEQ ID NO:2:

(i) SEQUENCE CHARACTERISTICS:
        (A) LENGTH: 1847 base pairs
        (B) TYPE: nucleic acid
        (C) STRANDEDNESS: single
        (D) TOPOLOGY: linear (xi) SEQUENCE DESCRIPTION: SEQ ID NO:2:

AGATCTCAAC CAGTTTAAAA TCGCACTTCA AGAAGTAAAA ATAGGGGCCG GCACCGGCTC       60

TTTTTTTGGT GTTTTTGTAG TTAGTGGATA TATCTGTTAG CTACAGAGAA AAGCGATTTT      120

AGAGGGTTTG ACGAGGTTTT TTCGAGCTAT CCAGGGTTTT TGGGTTTTTG GGGTTGGATC      180

AGAAAAGTCG TTCAAGATTA TTGACATAAA GACAGGAAGG TTTATAACAA GTACCAGATA      240

CGACAAAACC AGCTTTGCAG GCTGGCTTTG AAGGACTAAA AGAAGTGGGG ACTTCTTTGA      300

GTCTTGTAAT CAAGTTGGTC AGAACTCGAT TACGATTTGT AAGTAGAAAT CTAACTCACA      360

TTTCGCAGAA AGTCAAACTT ACCTCTTAGT TACAACTCAA AAATTTCCTA GCCTTTTCAG      420

ATCCTTAAGC ATACATATTT TGTTTAAACC GATTGTGTCC GGTGTTTGGT GTGGAGCCAT      480

TGATCCGAGT GGTCAATATG TGATTGTTCG CCAAACAGTG TATGTAGGTC TAAACGGGGA      540

GTGCTACAAA AGACCATACC CGAAACGAGT GCCTAAGTGT TTTGGTTATC AACCAGGTAA      600

GCTATGAGAA AGCCCAGCCA TAAATGGGGT TAGGTTGAAG CAAGTCTTCA TATGGTGCGA      660

CACAAGGGGT GTAGTAGGGT GTCGTCAAAC TGAAAGGTTT GATAGCTCTA AGCTTGTGCT      720

TCTGTGGGTC AAGCCTCAAG TGCTGATCTG TGGTGTCGTC TACCTGATAA CTTTCACTTT      780

TTCGAGTGAA ATTCAGGAGG CGAAACTATG GGTCAAGCCC AGCTTTGCTG GGGTTCGGCA      840

CATCCAGCTT ACAGCATTGG TGCTCTTGCG AAGCTGAAGC ACAAAAATCT AATCCAGGGT      900

TTGGGTTTTT TATACCAGAA GCAAACAAA AAATAAAAC AAAGAAAAAT TTCGAGCGA        960

AAAAATATTT TGGAATTTTT TAAAGGCGAT ACTTGCTACC GCACTTTTGC CATATTTAAA     1020

ACCTGACTAT CTTTATAAGT TAATAGATAT ATCCGTTAGA TTATAAAGTA TGTTAAAAAC     1080

GAGTAAAAAC AATAACTTAT ATATTTAATT CTGAATTATA TTTGACAGTG ATTATTTAAT     1140
```

-continued

| | |
|---|---|
| ATATTAAGAG ATATATCTAT TAGCTTAAAT ATAACTAAAA AAAGAGGTAA ATATATGGAT | 1200 |
| TGTGTATTTA AAAAAGCATT AGAAAATGAA ATAGAACATT ATAAAAAAGA CGGTGATATC | 1260 |
| AAATCTTTCT TACAATACTT GCATTACTTT GATATAGATA AAGCATTAAA TGGTGATGAA | 1320 |
| TGTGGCGATA TTATAAACTC AAATTTATCC ATTGATGAAA GTTTTGATCT TCTTGATGTT | 1380 |
| GAGCACAATT TCGGCTGGGC TTTCAATAAA ATAATACAGA GACGAAATGA ATATTTATCA | 1440 |
| TCAGCTAAAA CTGAAAATGA TTTTAAAAAA TACTCGTTCT TTATTCATTC GATCAATTGG | 1500 |
| GAAGAATTTA ATTACGATGA GATGAGTACA ATACATCAAG AAATGATTAA AGGATTAGAT | 1560 |
| AATTACACAT ATGGAGAAAT AACCATATGA ATAATAAAAT AAGAGAATAT ATTGATTTCG | 1620 |
| AAATAACAAA AGATATAAAA GAAAGTCAGC TCTTAAAAAT ATCTGCATTG ATCGATGTTT | 1680 |
| TAAAAGTAGA TGAAAAATTT ATTGATGAAG AGGATTTGCA ACTAAAGATA TTGAAAATAT | 1740 |
| CGTATGAAAA TCCTATTGAT GATCCAGATG ATGGCATAAG AAAATCACAA TTCGCACGAA | 1800 |
| GAAATGCCTA TGCTTTCCGC ATTAAAAAAA CAAGCAAAAA GAGATCT | 1847 |

(2) INFORMATION FOR SEQ ID NO:3:

(i) SEQUENCE CHARACTERISTICS:
        (A) LENGTH: 371 amino acids
        (B) TYPE: amino acid
        (C) STRANDEDNESS: single
        (D) TOPOLOGY: linear (xi) SEQUENCE DESCRIPTION: SEQ ID NO:3:

```
Asn Phe Leu His Trp Lys Phe Glu Lys Ile Arg Gln Lys Lys Leu Lys
 1               5                  10                  15

Trp Lys Lys Tyr Tyr Lys Lys Arg Arg Ser Asp Met Asp Phe Lys
            20                  25                  30

Ser Arg Lys Leu Thr Leu Asn Glu Lys Lys Asp Leu Glu Lys Ile Tyr
        35                  40                  45

Ala Glu Ser Glu Leu Lys Ala Lys Lys Leu Gly Thr Gln Pro Gly Val
    50                  55                  60

Val Leu Glu Met Thr Met Lys Glu Met Met Lys Asn Ile Asn Leu Asp
65                  70                  75                  80

Val Asn Glu Glu Thr Ala Gly Gln Tyr Arg Lys Leu Phe Lys Asn Lys
                85                  90                  95

Val Glu His Ser Lys Ser Asp Asp Leu Val Thr Gly Leu Leu Glu Cys
            100                 105                 110

Gly Thr Arg Asn Ser Phe Asp Lys Thr Arg Ser Ala Phe Arg Phe Cys
        115                 120                 125

Ile Cys Glu Arg Ile Gln Gln Leu Arg Lys Glu Ala Asp Asn Ala Arg
    130                 135                 140

Arg Val Lys Asp Phe Asp Thr Met Lys Ala Lys Thr Lys Glu Ala Phe
145                 150                 155                 160

Glu Leu Ser Phe Val Phe Asp Lys Asp Phe Leu Ser Glu Asn Arg Ile
                165                 170                 175

Gln Trp Asn Asp Ile Ser His Asn Lys Lys Asp Ser Ala Ser Lys Arg
            180                 185                 190

Lys Thr Met Lys Glu Ala Asp Thr Met Asp Asp Ile Phe Lys Arg Leu
        195                 200                 205

Lys Asn Asn Lys Ser Thr Tyr Asp Arg Tyr Ala Gly Phe Leu Ser Ile
    210                 215                 220

Cys Ser Ile Thr Gly Cys Arg Pro Ala Glu Val Leu Lys Gly Ile Glu
225                 230                 235                 240
```

-continued

```
Ile Val Arg Asn Arg Tyr Glu Asp Gly Ile Ser Phe Lys Ile Leu Gly
            245                 250                 255

Ala Lys Val Gly Asn Asp Arg Gly Gln Ser Glu Arg Thr Leu His Phe
            260                 265                 270

Asp Leu Ser Lys Tyr His Asp Asn Glu Gln Met Asn Tyr Ile Leu Ser
            275                 280                 285

Gln Leu Lys Asp Asn Lys Phe Phe Tyr Lys Pro Asp Gly Lys Leu Tyr
            290                 295                 300

Asn Ser Leu Arg Gln Tyr Leu Tyr Ile Gln His Arg Thr Phe Ser Leu
305                 310                 315                 320

Tyr Thr Leu Arg His Arg Val Ala Ser Asp Leu Lys Ala Ser Gly Ala
                325                 330                 335

Asp Asp Phe Thr Ile Ala Ala Xaa Leu Gly His Arg Val Thr Gln Ser
                340                 345                 350

Gln Glu Leu Leu Arg Leu Cys Ser Phe Val Xaa Arg Trp Tyr Arg Cys
            355                 360                 365

Asn Trp Cys
    370
```

US 6,916,646 B1

ENTEROBACTERIACEAE FERMENTATION STRAINS

FEDERALLY SPONSORED RESEARCH OR DEVELOPMENT

This invention was made with Government support under Grant No. 70NANB5H1138 awarded by Advanced Technology Program/National Institute of Standards and Technology. The Government has certain rights in this invention.

FIELD OF THE INVENTION

The present invention generally relates to improved fermentation strains of the family Enterobacteriaceae and specifically to methods for modifying phenotypic characteristics of the strains relevant to growth conditions. In particular, the present invention relates to the identification of a cryptic plasmid found within a strain of Enterobacteriaceae which modulates mobilization properties of other resident plasmids while providing advantageous growth characteristics.

BACKGROUND OF THE INVENTION

There are numerous commercially important compounds in the carbohydrate pathway of bacterial strains of the family Enterobacteriaceae including among others 2-KLG, a precursor to ascorbic acid; idonic acid; L-gluconic acid; and 2,5-DKG. Biocatalyic processes have been developed for the production of these compounds. In particular, Anderson et al., (1985, Science 230:144–149) disclose a metabolic pathway for Erwinia herbicola that permits the bioconversion of D-glucose to 2-KLG in a single fermentative step. In this bioconversion, there are a variety of intermediates and one step involves the reduction of 2,5-DKG to 2-KLG which is catalyzed by a recombinantly introduced NADPH-dependent 2,5-DKG reductase. In large scale fermentation of Enterobacteriaceae strains containing recombinantly introduced proteins there remain concerns of a regulatory nature associated with the recombinant nature of the organism.

Vladimir Dellic discloses a summary of a study of organisms for conversion of glucose to ketoacids on internet address "svibor@znanost.hr". This summary discloses the presence in Erwinia citreus ATCC accession number 31623 of a plasmid of 3.8 kb, designated pPZG500. Dellic discloses the introduction of a tetracycline resistance gene into pPZG500 which was used to clone a 2,5-DKG reductase gene.

There remains a need to develop improved Enterobacteriaceae fermentation strains that have desirable phenotypic characteristics relative to growth conditions and which minimize or eliminate the mobilization properties of resident plasmids under fermentation conditions.

SUMMARY OF THE INVENTION

The present invention generally relates to improved bacterial fermentation strains of the family Enterobacteriaceae. Specifically, the present invention relates to the identification and isolation of a 3.8 kb cryptic plasmid found in strains of Enterobacteriaceae. In a preferred embodiment, the Enterobacteriaceae strain is a recombinant strain.

The present invention is based in part upon the unexpected discovery that elimination of the cryptic plasmid from the Enterobacteriaceae strain Pantoea allows for growth of the organism at higher temperatures, thereby decreasing the time for production of desired compounds in the carbohydrate pathway. This discovery has the commercial benefit of potentially reducing both the capital cost and starting materials cost of large scale Enterobacteriaceae biocatalysis used in the production of desirable end-products, such as 2-keto-L-gluconic acid, a precursor of ascorbic acid.

The present invention is also based in part on the unexpected discovery that elimination of the cryptic plasmid from Pantoea reduces the mobilization properties of Pantoea resident plasmids thereby creating a safer and more desirable fermentation strain for the production of materials ultimately intended for human consumption, such as ascorbic acid.

The present invention provides a method for preparing an improved Enterobacteriaceae strain from a progenitor Enterobacteriaceae strain containing a cryptic plasmid, comprising the step of eliminating the cryptic plasmid from the progenitor strain thereby creating the improved strain. Preferably, the nucleic acid sequence of a 3.8 kb cryptic plasmid according to the invention comprises the plasmid designated herein as pS. The nucleic acid sequence of pS is provided herein and provides a means for identifying plasmids according to the invention which exist in Enterobacteriaceae species. The present invention also provides a method for reducing the mobilization properties of plasmids residing within a progenitor Enterobacteriaceae strain containing a cryptic plasmid comprising the step of eliminating part or all of the cryptic plasmid from the strain. In an alternative embodiment, the cryptic plasmid nucleic acid is mutated via recombinant DNA techniques to reduce the mobilization properties and/or produce the desirable growth characteristics.

In another embodiment, the present invention provides for an isolated nucleic acid having the sequence as shown in SEQ ID NO:1 and NO:2. In another embodiment, the present invention provides for an isolated amino acid as shown in SEQ ID NO:3. In yet another embodiment, the present invention provides a recombinant host cell produced by methods of the present invention. In one embodiment of the present invention, the host cell is an Enterobacteriaceae strain and in another embodiment, the host cell is Pantoea citrea having ATCC accession number 31940.

BRIEF DESCRIPTION OF THE DRAWINGS

FIGS. 1A–1F illustrates the nucleic acid sequence of cryptic plasmid designated herein as pS. The nucleic acid sequence is illustrated in two halves, SEQ ID NO: 1, FIGS. 1A–1C and SEQ ID NO: 2 FIGS. 1D–1F. The amino acid sequence corresponding to the largest open reading frame (SEQ ID NO:3) is translated in FIGS. 1A–1C.

FIG. 2 illustrates the growth at 28° C., 32° C., and 36° C. in ML5 media of a strain containing the cryptic plasmid (pS+) vs a strain that has been cured of the cryptic plasmid (pS−).

FIG. 3 illustrates the growth at 28° C., 32° C., and 36° C. in Luria broth of a strain containing the cryptic plasmid (pS+) vs a strain that has been cured of the cryptic plasmid (pS−).

DETAILED DESCRIPTION OF THE PREFERRED EMBODIMENTS

Definitions

As used herein, the family "Enterobacteriaceae" refers to fermentative bacterial strains having the general characteristics of being gram negative, oxidase-negative and being facultatively anaerobic. Preferred Enterobacteriaceae strains are those that are able to produce 2,5-diketo-D-gluconic acid from D-glucose solutions. Included in the family of Enterobacteriaceae which are able to produce 2,5-diketo-D-gluconic acid from D-glucose solutions are the genus *Erwinia, Enterobacter, Gluconobacter* and *Pantoea*, for example. Compounds of interest in the microbial carbohydrate pathway, include but are not limited to D-gluconate (GA), 2-keto-D-gluconate (2KDG), 2,5-diketo-D-gluconate (2,5DKG), 5DKG, 2-keto-L-gluconic acid (2KLG), L-idonic acid (IA) and ascorbic acid. In the present invention, a preferred Enterobacteriaceae fermentation strain is *Pantoea citrea* and preferred end compounds include idonic acid, 2KLG and ascorbic acid.

It is well understood in the art that the acidic derivatives of saccharides, may exist in a variety of ionization states depending upon their surrounding media, if in solution, or out of solution from which they are prepared if in solid form. The use of a term, such as, for example, gluconic acid, to designate such molecules is intended to include all ionization states of the organic molecule referred to. Thus, for example, both "D-gluconic acid" and "D-gluconate" refer to the same organic moiety, and are not intended to specify particular ionization states. The present invention encompasses the unionized forms of derivatives of saccharides, such as, for example, the sodium, potassium or other salt.

As used herein, the phrase "progenitor strain" refers to an Enterobacteriaceae strain containing a cryptic plasmid. The term "cryptic plasmid" refers to a plasmid found naturally occurring in a Enterobacteriaceae strain which when deleted from the progenitor strain alters the phenotypic growth characteristics or alters mobilization properties of other Enterobacteriaceae resident plasmids.

A preferred cryptic plasmid is designated herein as "pS" and refers to a 3.8 kb nucleic acid having the sequence as depicted in SEQ ID NO:1 and SEQ ID NO:2. However, the present invention further encompasses homologs and variations of SEQ ID NO:1 and SEQ ID NO:2 that retain at least one functional characteristic associated with SEQ ID NO:1 and NO:2, i.e., improved phenotypic growth characteristics or reduction of resident plasmid mobilization properties. Due to the degeneracy of the genetic code, a variety of nucleic acids could encode a deduced amino acid sequence encoded by an open reading frame present in SEQ ID NO: 1 and SEQ ID NO:2. Cryptic plasmids according to the present invention encompasse all such nucleic acid variations.

Preferred nucleic acid homologs or variations are those having at least 80%, at least 90% and at least 95% identity to SEQ ID NO: 1 and SEQ ID NO:2. Preferred nucleic acid homologs or variations hybridize under high stringency conditions. The deduced amino acid sequence (SEQ ID NO:3) encoded by the open reading frame shown in SEQ ID NO:1 is illustrated in FIGS. 1A–1C.

As used herein, the term "recombinant" refers to an Enterobacteriaceae strain that contains nucleic acid not naturally occurring in the strain which has been introduced into the strain using recombinant techniques.

As used herein, the term "improved" when referring to an industrial fermentation strain means a strain having at least one desirable phenotypic modification of the progenitor strain. Illustrative of such desirable phenotype modifications include ability to grow at higher temperatures, increased growth rate upon fermentation at higher temperatures and loss of mobilization of plasmids residing within the strain.

The property of "mobilization" as used herein refers to the transmissibility of a plasmid residing within a fermentation strain.

As used herein the phrase "eliminating the cryptic plasmid from the fermentation strain" refers to the process of curing a fermentation strain of a cryptic plasmid. The present invention also encompasses modifications of the cryptic plasmid nucleic acid made through recombinant means, such as deletions, insertions, mutations, which interrupt the plasmid and its function in the host cell.

Oxidative enzymes associated with the biocatalysis of D-glucose to pathway intermediates include D-glucose dehydrogenase, D-gluconate dehydrogenase and 2-keto-D-gluconate dehydrogenase. Reductive enzymes associated with the biocatalysis of pathway intermediates into desired end-products include 2,5-diketo-D-gluconate reductase (DKGR), 2-keto reductase (2-KR) and 5-keto reductase (5-KR). Such enzymes include those produced naturally by the host strain or those introduced via recombinant means.

As used herein, the term "heterologous" refers to proteins such as enzymes that are not naturally present in host industrial fermentation strains but which have been introduced through recombinant DNA technology.

As used herein, the term fermentation refers to the range of 10 L to 500,000 L cultures.

Description of the Preferred Embodiments

The present invention relates to the identification and isolation of a cryptic plasmid from a strain of the family Enterobacteriaceae. Eliminating this plasmid from the Enterobacteriaceae strain reduced the mobilization properties of a resident plasmid, allowed the organism to grow at higher temperatures than the progenitor strain and provides a means for producing desirable end products in shorter fermentation runs thereby reducing the cost of their production. The following is a description of a preferred embodiment. The techniques disclosed herein are applicable to other embodiments of the present invention.

I. Biocatalysis

The present invention encompasses strains of the family Enterobacteriaceae. Preferred strains of the family Enterobacteriaceae are those that produce 2,5-diketo-D-gluconic acid from D-glucose solutions, including *Pantoea*, are described in Kageyama et al. (1992, International Journal of Systematic Bacteriology vol. 42, p. 203–210). The metabolic pathway of carbohydrate metabolism in recombinant 2-KLG producing strains is disclosed in Lazarus et al. (1990, Proceedings $6^{th}$ international Symposium on Genetics of Industrial Microorganisms, Strasbourg, Vol. II 1073–1082).

Biocatalysis begins with a suitable carbon source ordinarily used by Enterobacteriaceae strains, such as glucose. Other metabolite sources include, but are not limited to galactose, lactose, fructose, or the enzymatic derivatives of such. In addition to an appropriate carbon source, fermentation media must contain suitable minerals, salts, cofactors, buffers and other components, known to those of skill in the art for the growth of cultures and promotion of the enzymatic pathway necessary for production of desired end-products.

In one illustrative *Pantoea* pathway, D-glucose undergoes a series of oxidative steps through enzymatic conversions, which may include the enzymes D-glucose dehydrogenase, D-gluconate dehydrogenase and 2-keto-D-gluconate dehydrogenase to give intermediates which may include, but are not limited to GA, 2KDG, and 2,5-DKG, see U.S. Pat. No. 3,790,444. These intermediates undergo a series of reducing steps through enzymatic conversions, which may include the enzymes 2,5-diketo-D-gluconate reductase (DKGR), 2-keto reductase (2-KR) and 5-keto reductase (5-KR) to give end products which include but are not limited to 2KLG and IA.

The present invention also encompasses other metabolic pathways and intermediates naturally occurring in or recombinantly introduced into Enterobacteriaceae strains, such as for example, a pathway that proceeds through the intermediate sorbitol.

In a preferred embodiment of the present invention, the preferred fermentation strain is *Pantoea citrea*, ATCC accession number 39140. The present invention encompasses the production of desired pathway end products obtained entirely through in vivo methods or combined in vivo/in vitro methods.

II. Recombinant Introduction of Enzymes into Fermentation Strains

Any enzymes necessary for directing a Enterobacteriaceae strain carbohydrate pathway into desired end-products can be introduced via recombinant DNA techniques known to those of skill in the art if such enzymes are not naturally occurring. Alternatively, enzymes that would hinder a desired pathway can be deleted by recombinant DNA methods. The present invention includes the recombinant introduction or deletion of any enzyme or intermediate necessary to achieve a desired pathway. As used herein, recombinant DNA technology includes in vitro recombinant DNA techniques, synthetic techniques and in vivo recombinant/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing "Associates and Wiley Interscience, N.Y.

In one embodiment of the present invention, nucleic acid encoding DKGR is recombinantly introduced into the *Pantoea* fermentation strain. Many species have been found to contain DKGR particularly members of the Coryneform group, including the genera *Corynebacterium*, *Brevibacterium*, and *Arthrobacter*.

In one preferred embodiment of the present invention, 2,5-DKGR from *Corynebacterium* sp. strain SHS752001 (Grindley et al., 1988. *Applied and Environmental Microbiology* 54: 1770–1775) is recombinantly introduced into a *Pantoea citrea* and the desired end product is 2KLG, a precursor to ascorbic acid. Production of recombinant 2,5 DKG reductase by *Erwinia herbicola* is disclosed in U.S. Pat. No. 5,008,193 to Anderson et al.

A preferred plasmid for the recombinant introduction of non-naturally occurring enzymes or intermediates into a strain of Enterobacteriaceae is RSF1010, a mobilizable, but not self transmissible plasmid which has the capability to replicate in a broad range of bacterial hosts, including Gram− and Gram+ bacteria. (Frey et al., 1989, The Molecular biology of IncQ plasmids. In: Thomas (Ed.), *Promiscuous Plasmids of Gram Negative Bacteria*. Academic Press, London, pp. 79–94). Frey et al. (1992, Gene 113:101–106) report on three regions found to affect the mobilization properties of RSF1010. In a preferred embodiment, mobilization defective RSF1010 mutants are used for the recombinant introduction of non-naturally occurring enzymes into Enterobacteriaceae strains that have been cured of a cryptic plasmid.

III. Growth Conditions

Typically Enterobacteriaceae host cells are grown in the range of about 28° C. to about 37° C. in appropriate culture media. General growth conditions are disclosed in Truesdell et al., (1991, Journal of Bacteriology, 173: 6651–6656) and Sonoyama et al. (1982, Applied and Environmental Microbiology, vol. 43, p. 1064–1069). *Pantoea citrea* ATCC accession number 39140 has a nicotinic acid growth requirement which can be provided by nicotinomide at 100 μg/ml (Sigma). Culture media may be supplemented by the presence of selectable markers such as antibiotic resistance genes, including but not limited to tetracycline, ampicillin or chloramphenicol.

Three physical parameters which affect fermentation performance include dissolved oxygen content, pH and temperature. The rate of oxidation of metabolite sources can be limited by oxygen availability. However, the oxidation reaction will go to completion as long as oxygen is continually supplied to the culture media. In *Pantoea citrea* fermentation, air is continually provided to the fermentation tanks.

The genera *Pantoea* maintains metabolic activity under a wide range of pH conditions. Preferred pH is in the range of 4.0 to 7.5. Table 1 discloses the pH optimum for desired pathway conditions of *Pantoea citrea*.

TABLE 1

| Condition | pH Opt. |
|---|---|
| 1. Growth | 6.0–<7.5 |
| Glucose to 2-KDG (Ox.) | 4.0–5.5 |
| 2-KDG to 2,5 DKG (Ox.) | 5.0–5.5 |
| 2,5 DKG to 2-KGA (Red.) | 5.5–6.0 |
| 2-KGA to Idonate (Red.) | 6.5–7.5 |
| Idonate to 2-KGA (Ox.) | 5.5–6.5 |

Several combinations of acid and base can be used for pH control, including but not limited to, phosphoric acid, sulfuric acid, hydrochloric acid, sodium bicarbonate, calcium carbonate, sodium hydroxide, ammonium hydroxide, and calcium hydroxide.

The optimum growth temperature of *Pantoea citrea* ATCC accession number 39140 containing the cryptic plasmid is 28 to 30° C. In ATCC accession number 39140 that has been cured of the cryptic plasmid, growth can occur at temperatures above 30° C. up to about 36° C. FIGS. 2 and 3 illustrate the growth characteristics at 28° C., 32° C., 36° C. of a pS+ strain vs a pS− strain. The growth differential between pS+ and pS− strains appears more pronounced in minimal media conditions. Accordingly, the present invention provides the unexpected advantage of providing a method for producing improved fermentation strains that can grow at higher temperatures under minimal media conditions, thereby reducing the overall cost of fermentation, i.e., production of end products. Because the kinetic parameters for various enzymes in the carbohydrate metabolism pathway may be affected by elevated temperatures, the relative ratios of end-products may be affected. Accordingly, another unexpected advantage of culturing a pS− strain under elevated temperatures is to affect a shift in the ratios of end-products.

Biocatalysis end products can be measured by HPLC analysis of the fermentation broth with standard concentrations being used as controls.

IV. Nucleic Acid Identification Methods

Means for identifying a cryptic plasmid nucleic acid within a Enterobacteriaceae species include hybridization screening techniques that use radioactive or enzymatically labeled probes to screen the suspect species nucleic acid under high stringency conditions. The term probe refers to a portion, fragment or segment of SEQ ID NO:1 or SEQ ID NO:2 that is capable of being hybridized to a desired target nucleotide sequence and probes can be used to detect, amplify or quantify nucleic acid. Probes may be labeled by nick translation, Klenow fill-in reaction, PCR or other methods well known in the art.

Alternatively, polymerase chain reaction (PCR) based strategy (U.S. Pat. Nos. 4,683,195; 4,800,195; 4,965,188) may be used to identify nucleic acid of the cryptic plasmid. Oligonucleotides preferably in the range of 18–22 nucleotides derived from SEQ ID NO:1 or SEQ ID NO:2 serve as primers for the PCR reaction with the template comprising nucleic acid derived from suspect *Pantoea* species. Any PCR products or other identified nucleic acid may be subcloned and subjected to nucleic acid sequencing to confirm the identity of the cryptic plasmid.

Methods for nucleic acid sequencing are well known in the art. Conventional enzymatic methods employ DNA polymerase Klenow fragment, SEQUENASE® (US Biochemical Corp, Cleveland, Ohio) or Taq polymerase to extend DNA chains from an oligonucleotide primer annealed to the DNA template of interest.

The cryptic plasmid pS was sequenced in two parts and is shown in SEQ ID NO:1 and SEQ ID NO:2. Scientific programs such as, DNASTAR (DNASTAR Inc., 1228 South Park St., Madison, Wis. 53715) are available to those of skill in the art for joining the two sequences, SEQ ID NO:1 and SEQ ID NO:2, in order to obtain a continuous sequence.

V. Methods for Curing Enterobacteriaceae Strains of the Cryptic Plasmid

Methods for curing the cryptic plasmid from Enterobacteriaceae are described in Jeffrey Miller (1972, in Curing of Episomes from *E.Coli* strains with Acridine Orange from Experiments in Molecular Genetics, Cold Spring Harbor Laboratories, pg. 140). In this method, acridine orange is added to 5 ml cultures of an Enterobacteriaceae strain at 125 µg/ml and allowed to grow overnight at 37° C. The following day, the cultures are plated out and individual colonies are used to prepare plasmid nucleic acid. The nucleic acid is analysed by means known to those of skill in the art to determine the presence or absence of the plasmid.

The manner and method of carrying out the present invention may be more fully understood by those of skill in the art by reference to the following examples, which examples are not intended in any manner to limit the scope of the present invention or of the claims directed thereto.

EXAMPLES

I. Identification of the Cryptic Plasmid.

This example describes the initial discovery and identification of pS in *Pantoea citrea*. pS was discovered during a plasmid purification experiment specifically designed to find any cryptic plasmids native to the *Pantoea citrea*.

*Pantoea citrea* ATCC accession number 39140 was subjected to a plasmid preparation by standard means. Plasmid DNA was subjected to 1% agarose gel electrophoresis and a plasmid of 3.8 kb, designated pS, was identified. The 3.8 kb band was excised and the nucleic acid was electroeluted and purified by precipitation. pS nucleic acid was subjected to restriction analysis via restriction endonucleases and sequenced by standard dideoxy sequencing methodology. The nucleic acid sequence of pS is shown in two halves, SEQ ID NO:1 and SEQ ID NO:2. SEQ ID NO:1 and SEQ ID NO:2 were subjected to a BLAST search (FastA Genetics Computer Group, Inc., University Research Park, 575 Science Dr. Ste. B, Madison, Wis. 53711) which revealed no homology to known nucleic acids. The amino acid sequence encoding by the largest open reading frame is shown in FIGS. 1A–1C and is designated SEQ ID NO:3.

II. Curing *Pantoea citrea* of pS.

This example describes the method for curing *Pantoea citrea* of pS.

Acridine orange was added to 5 ml cultures of *Pantoea citrea* ATCC accession number 39140 at 125 µg/ml and allowed to grow overnight at 37° C. The following day, the cultures were plated out and individual colonies were used to prepare plasmid nucleic acid. The nucleic acid thus prepared was analysed on a 1% agarose gel to determine the presence or absence of pS. One colony was determined to no longer contain pS. Subsequent purification of the colony and repeated efforts to isolate the plasmid DNA confirmed that this particular isolate had lost the cryptic plasmid. This culture, designated as *Pantoea citrea* pS– or "pS–" was used for subsequent experimentation in comparisons with *Pantoea citrea* containing pS or "pS+"

III. Transmissibility of Vector Plasmids from *Pantoea citrea* to other Microbial Hosts.

The purpose of this example was to determine the transfer frequency of expression vectors from *Pantoea citrea* to *Escherichia coli* and *Pseudomonas aeruginosa*. Transfer frequency was assayed by mating strains of *Pantoea citrea* with *E coli* and *P.aeruginosa* under selective conditions and in the presence of a counter selective agent or condition.

An expression vector containing nucleic acid encoding a DGKR was created using plasmid RSF1010 which was modified by deleting a region of the plasmid involved in mobilization (Frey et al., supra). Additionally, the cryptic plasmid, was cured from *Pantoea citrea* by the method disclosed in Example II.

Materials and Methods

*E.coli* strain 294 (endA, hsdR, Thi⁻, Pro⁻, Str$^S$) was used as the recipient in all the experiments pertaining to *E.coli*. Selective conditions included Tetracycline at 20 and 100 µg/ml and Streptomycin at 100 and 500 µg/ml. Counter selective agents or conditions include growth at 42° C. or the presence of Irgasan at 12 µg/ml. The selective temperature conditions were chosen to be 37° C., however, it was determined that the two *Pantoea citrea* strains having been cured of the cryptic plasmid were able to grow at 37° C. the *Pantoea citrea* strain that contained the cryptic plasmid (pS–) was still unable to grow at 37° C. Accordingly, all *P. citrea* strains were tested for growth at 42° C. All three *P. citrea* strains failed to grow at this temperature under the conditions used for selection, while the recipient *E. coli* strain was able to grow at this temperature. The same conditions were used for *P. aeruginosa* as used for *E. coli*. Table II illustrates the selective and counterselective conditions used for experimentation.

TABLE 2

SELECTIVE AND COUNTERSELECTIVE AGENTS AND CONDITIONS

| MATING | SELECTIVE ANTIBIOTIC | COUNTER SELECTIVE AGENT OR CONDITION |
|---|---|---|
| *P. citrea* –pS (pD92) × *E. coli* 294 | Tetracycline 20 µg/ml | Growth @ 42° C. |
| *P. citrea* –139-2A (Δ18) × *E. coli* 294 | Streptomycin 100 µg/ml | Growth @ 42° C. |
| *P. citrea* –pS (Δ18) × *E. coli* 294 | Streptomycin 100 µg/ml | Growth @ 42° C. |
| *P. citrea* –pS (pD92) × *P. aeruginosa* PA01 | Tetracycline 100 µg/ml | Irgasan 12 µg/ml |
| *P. citrea* –139-2A (Δ18) × *P. aeruginosa* PA01 | Streptomycin 500 µg/ml | Irgasan 12 µg/ml |
| *P. citrea* –pS (Δ18) × *P. aeruginosa* PA01 | Streptomycin 500 µg/ml | Irgasan 12 µg/ml |

Mating

Each strain of *Pantoea citrea* was mated with *E.coli* 294 and *P. aeruginosa* PA01 on three separate occasions. As a negative control, each strain of *P. citrea* was used in a mock mating without a recipient. No growth was observed on any of the selective plates in these mock matings.

The frequency of transfer was calculated as follows:

Frequency of transfer (%)=#Transconjugants/ml×100 ∩Input Donor/ml

The data from all matings are shown in Table 3.

TABLE 3

FREQUENCY OF TRANSMISSION OF VECTOR PLASMIDS
TO E. COLI 294 AND P. AERUGINOSA PA01

| Mating | Exp. 1 | Exp. 2 | Exp. 3 | Mean |
|---|---|---|---|---|
| P. citrea –pS (pD92) × E. coli 294 | .001% | .0003% | .0008% | .0007% |
| P. citrea –139-2A (Δ18) × E. coli 294 | .0017% | .0002% | .0005% | .0008% |
| P. citrea –pS (Δ18) × E. coli 294 | .0009% | .0002% | .00007% | .0004% |
| P. citrea –pS (pD92) × P. aeruginosa PA01 | .0006% | .0001% | .00003% | .0002% |
| P. citrea –139-2A (Δ18) × P. aeruginosa PA01 | .0001% | .0003% | .0001% | .0002% |
| P. citrea –pS (Δ18) × P. aeruginosa PA01 | .0003% | .00015% | .0001% | .0002% |

Analysis of Transconjugants

Because of the very low apparent frequency of transmission that was observed genetically, it was necessary to examine transconjugants for the presence of vector plasmids to determine whether transmission had actually occurred or whether the colonies observed on the selection plates were due to selection of chromosomal mutations that result in resistance to the antibiotics used. 10 transconjugants from each mating were examined for the presence of plasmids. Plasmids were detected in all cases.

Results

The results shown in Table 3 indicate that transmission of the expression vector from P. citrea cured of the small cryptic plasmid (pS–) to E. coli and P. aeruginosa has been reduced about 1000 fold in comparison to P. citrea having the small cryptic plasmid present.

Transmission of RSF1010 based expression vector having the deletion disclosed in Frey et al., supra, to E coli and P. aeruginosa from P. citrea was reduced by about 1000 fold in comparison to transmission of the RSF1010 plasmid without the mutation to these organisms from P. citrea.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated in their entirety.

What is claimed is:

1. A method for obtaining an improved Enterobacteriaceae strain comprising,
   a) obtaining a progenitor strain from the genera of *Pantoea, Enterobacter, Erwinia* or *Gluconobacter*, and
   b) eliminating a cryptic plasmid from the progenitor strain to obtain an improved strain
   said cryptic plasmid having a nucleic acid sequence of at least 95% sequence identity with SEQ ID NO:1 and SEQ ID NO:2 and wherein the improved strain is able to grow at higher temperatures than the progenitor strain.

2. The method according to claim 1, wherein the progenitor strain is capable of producing 2,5-diketo-D-gluconate from a carbon source.

3. The method according to claim 1, wherein the progenitor strain is a recombinant strain that comprises a heterologous nucleic acid sequence encoding a 2,5,-diketo-D-gluconate reductase and is capable of converting 2,5-diketo-D-gluconate to 2-keto-L-gluconic acid.

4. The method according to claim 1, wherein an open reading frame of the nucleic acid sequence of the cryptic plasmid encodes an amino acid sequence having the sequence of SEQ ID NO:3.

5. The method according to claim 1, wherein the cryptic plasmid has the nucleic acid sequence shown in SEQ ID NO:1 and SEQ ID NO:2.

6. A method for reducing the mobilization properties of plasmids residing within an Enterobacteriaceae strain comprising,
   a) obtaining an Enterobacteriaceae progenitor strain from the genera of *Pantoea, Enterobacter, Erwinia* or *Gluconobacter*, which includes a cryptic plasmid having a nucleic acid sequence of at least 95% sequence identity with SEQ ID NO:1 and SEQ ID NO:2, and
   b) eliminating the cryptic plasmid.

7. The method according to claim 6, wherein the progenitor strain is capable of producing 2,5-diketo-D-gluconate from a carbon source.

8. The method according to claim 6, wherein the progenitor strain is a recombinant strain that comprises a heterologous nucleic acid sequence encoding a 2,5-diketo-D-gluconate reductase and is capable of converting 2,5-diketo-D-gluconate to 2-keto-L-gluconic acid.

9. A method for obtaining an improved *Pantoea* strain comprising,
   a) obtaining a *Pantoea* progenitor strain which includes a cryptic plasmid, said cryptic plasmid having a nucleic acid sequence with at least 95% sequence identity to SEQ ID NO:1 and SEQ ID NO:2, and
   b) eliminating the cryptic plasmid from the *Pantoea* strain thereby obtaining an improved *Pantoea* strain,
   wherein the improved strain is able to grow at a higher temperature than the progenitor strain.

10. The method according to claim 9, wherein the *Pantoea* progenitor strain is a *Pantoea citrea* strain.

11. The method according to claim 9, wherein the *Pantoea* progenitor strain is a recombinant strain.

12. The method according to claim 1, wherein said improved strain is a *Pantoea* strain.

13. The method according to claim 9, wherein the cryptic plasmid has the nucleic acid sequence of SEQ ID NO:1 and SEQ ID NO:2.

14. A method for obtaining an improved *Pantoea* strain comprising,
   a) obtaining a *Pantoea* progenitor strain which includes a cryptic plasmid, said cryptic plasmid having a nucleic acid sequence of at least 95% sequence identity to the nucleic acid sequence of SEQ ID NO:1 and SEQ ID NO:2 which encodes a polypeptide having the sequence of SEQ ID NO: 3, and
   b) eliminating the cryptic plasmid from the *Pantoea* progenitor strain thereby obtaining an improved *Pantoea* strain.

15. The method according to claim 14, wherein the *Pantoea* progenitor strain is a *P. citrea* strain.

16. The method according to claim 14, wherein the improved *Pantoea* strain is able to grow at a higher temperature than the progenitor strain.

* * * * *